United States Patent [19]

Fischer

[11] Patent Number: 5,785,955
[45] Date of Patent: Jul. 28, 1998

[54] HEMOSTATIC COMPOSITIONS FOR TREATING SOFT TISSUE

[76] Inventor: Dan E. Fischer, 10444 S. Dimple Dell Rd., Sandy, Utah 84093

[21] Appl. No.: 926,866

[22] Filed: Sep. 10, 1997

Related U.S. Application Data

[63] Continuation of Ser. No. 439,856, May 12, 1995, abandoned, which is a continuation of Ser. No. 393,369, Feb. 23, 1995, Pat. No. 5,635,162.

[51] Int. Cl.$^6$ ............................................. A61K 9/68
[52] U.S. Cl. ............................................. 424/49
[58] Field of Search ............................................. 424/49

[56] References Cited

U.S. PATENT DOCUMENTS

| | | |
|---|---|---|
| 459,738 | 9/1891 | Blask . |
| 2,209,454 | 7/1940 | Guest . |
| 2,322,735 | 6/1943 | Molnar . |
| 2,411,636 | 11/1946 | Preiswerk . |
| 4,260,597 | 4/1981 | Porteous ............ 424/49 |
| 4,395,398 | 7/1983 | Yamamoto ............ 424/145 |
| 4,551,100 | 11/1985 | Fischer ............ 433/218 |
| 4,578,055 | 3/1986 | Fischer . |
| 4,617,950 | 10/1986 | Porteous et al. ............ 424/49 |

FOREIGN PATENT DOCUMENTS 2224652 5/1990 United Kingdom .

OTHER PUBLICATIONS

*Carbowax Polyethylene Glycols*, Union Carbide Industrial Chemicals Division, Product Information Bulletin (1986).

Charbeneau, Gerald T., D.D.S. et al., "Chemical Tissue Packes," *Principles and Practice of Operative Dentistry*, pp. 390–391, Lea & Febiger (1975).

Fischer, Dan, D.D.S., "Chapter 15: Tissue Management for Making Impressions," *Restorative Techniques for Individual Teeth*, edited by Lloyd Baum, pp. 247–265, Masson Publ. (1981).

Fischer, Dan D.D.S., "Tissue Management: A New Solution to an Old Problem," Academy of General Dentistry (1987).

Gilmore, H. William, D.D.S., et al., "Indirect Procedures for Case Construction," *Operative Dentistry*, p. 264, 3rd Ed., C.V. Mosby Co. (1977).

Gurney, B. Franklin, D.D.S., "Hemostatic Agents, Part I," *Chemotherapy and the Dentist*, pp. 74–86 (1966).

Leer, Jerry H., D.D.S., et al., "Management of Gingival Tissue during Indirect Impression Procedures," *JADA*, pp. 924–928, vol. 75 (Oct. 1967).

Woycheshin, Felix F., D.D.S., "An Evaluation of the Drugs Used for Gingival Retraction," *J. Pros. Den.*, pp. 769–776 (Jul.–Aug. 1964).

"Gingival Tissue Management," *Current Therapy in Denistry*, edited by Goldman et al., vol. 4, pp. 272–273, C.V. Mosby Co. (1970).

"Hemostatics and Astringents," *Accepted Dental Therapeutics*, 39th Ed., p. 286 (1992).

"Iron and Iron Compounds," *Accepted Dental Remedies*, pp. 119–121, Council on Dental Therapeutics, American Dental Association (1934).

"Results of the First CRA Consumer Opinion Survey," Clinical Research Associates Newsletter, vol. 3, Issue 8 (Aug. 1979).

*Primary Examiner*—Paul J. Killos
*Attorney, Agent, or Firm*—Workman, Nydegger & Seeley

[57] ABSTRACT

A hemostatic composition for controlling oral bleeding or providing gingival tissue fluid control, which includes a hemostatic agent, a chemical agent for reducing the acidic activity of the hemostatic agent, and an aqueous base. The hemostatic compositions are useful in treating wounds in soft tissues in general. The hemostatic composition can be used to stop bleeding or control gingival tissue fluid flow without opening up the dentinal tubules in the dentin of a tooth that has been cut during dental restorative and reconstructive procedures. The hemostatic composition is also less aggressive and more gentle when used to treat wounds in soft tissues in general. The chemical agent is preferably an inorganic filler or high molecular weight polyol that reduces the acidic or other chemical activity of the hemostatic agent. This allows the smear layer plugs in the dentinal tubules to remain substantially intact to occlude passage of potentially harmful contaminants into the tubules and hence into the dental pulp. It also reduces inflammation and other irritating affects in soft tissue when using the hemostatic composition.

43 Claims, No Drawings

HEMOSTATIC COMPOSITIONS FOR TREATING SOFT TISSUE

This application is a file-wrapper-continuation of U.S. application Ser. No. 08/439,856, filed May 12, 1995, abandoned, which is a continuation of U.S. application Ser. No. 08/393,369, filed Feb. 23, 1995, now U.S. Pat. No. 5,635,162.

BACKGROUND OF THE INVENTION

1. The Field of the Invention

The present invention relates to hemostatic compositions and methods for their use in dental procedures. More particularly, the present invention is directed to an improved hemostatic dental composition that can be applied to the gingival area of a tooth. In addition, the hemostatic compositions are more gentle and less aggressive when used to treat any soft tissue.

2. The Related Technology

The development of modern instrumentation and materials, together with increased public awareness of the desirability of tooth preservation, have made cast restorations vital and frequently used elements in restorative and reconstructive prosthodontics dentistry. For years dentists have relied on indirect cast restorations such as crowns to maximize function, integrity, and aesthetics for compromised teeth. A primary concern during cast restoration procedures is the controlling of oral bleeding while taking impressions of teeth for reconstruction. During dental reconstruction or preparation of dental crowns, it is common for dentists to cut gingival or gum tissue in order to fully expose the tooth prior to taking an impression of the tooth. It is imperative that the area surrounding the tooth be clean and dry for an accurate impression to be made. To this end, various astringent or hemostatic agents have been used to stop bleeding.

Most failures of cast restorations can be ascribed to poor marginal fit. A primary reason for poor marginal fit is incomplete reproduction of marginal detail in the impression. That defect, in turn, usually may be attributed to poor tissue management. Poor tissue management is the weak link in fixed prosthodontics. Dentists are continually presented with improved techniques and materials that are dependent upon predictable tissue management for successful results. Tissue management during impression making has traditionally centered on chemical and mechanical means of controlling bleeding plus creating a horizontal and vertical space for the impression material. Controlling tissues is the most important step towards the attainment of a precise fitting for subgingival margins.

Many materials and devices have been proposed for horizontal and vertical retraction of soft tissue and hemorrhage control. Unfortunately, undesirable systemic and local side effects are caused by some of the most effective materials. Such side effects have produced frustration for the dentist and discomfort for the patient.

With the increase of near gingival and/or subgingival bonded restorations, there has arisen an intense need to obtain highly effective sulcular fluid control prior to starting the bonding procedure. Modern adhesive dentistry allows dentists to intimately bond porcelain crowns, inlays, veneers and other materials directly to enamel and dentin. Needless to say, extraneous oral fluids preclude success whether for impression making or adhesive dentistry. Complete tissue and sulcular fluid control must occur prior to enamel and dentin bonding procedures when bonding near or under sulcular tissues.

Various hemostats and astringents have been used in dental procedures to control bleeding and aid in retraction of tissue. One of the most common hemostatic and retraction agents used in dentistry is an aqueous solution of aluminum chloride, marketed under a variety of tradenames by several manufacturers. Ferric salts have also been used as astringents, such as ferric subsulfate (Monsel's solution), ferric sulfate, and ferric chloride. A ferric sulfate solution is disclosed in U.S. Pat. No. 4,551,100, for use in the gingival area as a hemostatic agent having both coagulant and astringent properties. The solution was prepared from aqueous ferric sulfate having a concentration of about 6 to 20% in water and glycol. An astringent gel is disclosed in U.S. Pat. No. 4,617,950, which includes an astringent salt and a bodying agent such as carboxypolymethylene.

In order to apply a prosthetic dental device such as a crown to a tooth, the enamel covering the dentin of the tooth must be cut in order to prepare a surface for application of the crown. Typically, a diamond bur is used on a dental drill that rotates at high speed to enable a dentist to cut by grinding the tooth. A newly cut tooth has a smear layer on the surface of the dentin, which is the semi-attached, semi-fractured residue from cutting the tooth, and includes a semi-attached layer of collagen fibrils. Part of the smear layer enters the dentinal tubules, which open at the surface of the dentin, and forms plugs that occlude the tubules. The smear layer plugs in the dentinal tubules can act as a barrier which can prevent contaminants from entering the tubules and infecting the tooth.

A problem that has been encountered in performing the procedures required for dental restorations has been that the smear layer plugs can be opened up in the dentinal tubules by liquid astringents used to stop bleeding in the gingival area. An astringent or hemostat is typically introduced into the sulcus of a tooth to stop bleeding, but can flow over the top of a tooth and contact exposed dentin. If the astringent or hemostat is too harsh or acidic, it can dissolve the smear layer plugs in the dentinal tubules, allowing harmful contaminants such as bacteria to enter the tooth. The acidic and/or other inherent chemical nature of the astringents has also caused a caustic and unpleasant taste in a patient's mouth during treatments.

In general, hemostatic compositions can cause inflammation and other deleterious tissue responses that can slow the healing process and cause patient discomfort when used to treat wounds and soft tissue. This is also due to the acidic and/or other inherent chemical nature of astringents used to check bleeding.

SUMMARY AND OBJECTS OF THE INVENTION

The present invention is directed to improved hemostatic dental compositions that include in an aqueous base, a hemostatic agent that provides astringent action for stopping oral bleeding or providing gingival tissue fluid control, and a chemical binding or coating agent for reducing the acidic activity of the hemostatic agent sufficient to reduce substantial removal of the smear layer plugs in the dentinal tubules of a tooth. Use of the hemostatic composition during dental restorative and reconstructive procedures stops oral bleeding and provides gingival tissue fluid control without opening up the dentinal tubules in the dentin. In addition, the hemostatic compositions appear to be more gentle and less aggressive when used to treat wounds in any soft tissue.

The chemical binding or coating agent can be selected from an inorganic filler, a high molecular weight polyol, or mixtures thereof. This chemical agent absorbs, loosely binds, or coats the hemostatic agent, preventing the acidic nature of the active chemical ingredient of the hemostatic agent from significantly dissolving the smear layer plugs in the dentinal tubules and minimizing any harmful chemical effects of the hemostatic agent. The smear layer plugs in the dentinal tubules thus remain substantially intact to occlude passage of harmful contaminants into the tubules, thereby preventing sensitivity and/or infection of the tooth. In addition, the chemical binding agent is apparently responsible for making the hemostatic composition less aggressive on soft tissues in general. The chemical agent also reduces the unpleasant taste of the hemostatic agent in the composition during treatments therewith. When the composition of the invention is agitated, the hemostatic agent is loosened from the chemical agent binding or tying up the hemostatic agent, resulting in increased activity of the hemostatic agent at the point of agitation.

The hemostatic composition of the invention is a viscous solution, which helps to keep the composition in place when applied from an applicator device. A preferred hemostatic agent is a ferric salt compound such as ferric sulphate, although other hemostats may be utilized in the composition of the invention. Ferric salts are coagulative hemostats in that they form a coagulum when contacted with blood. When an inorganic filler is used to reduce the acidic effect of the hemostatic agent, preferably a silica-based absorbing agent is used, although other inorganic fillers may also be employed. When polyols are used to reduce the acidic effect of the hemostatic agent, preferably high molecular weight glycols are utilized in the composition of the invention.

The composition of the invention can be used in a system for controlling oral bleeding and gingival tissue fluid flow, which includes an applicator device capable of applying the dental composition under pressure to an area of bleeding or fluid leaking gingival tissue. The applicator device has a padded porous tip through which the composition may be applied and is preferably a Dento-Infusor device. The applicator device can be used with the dental composition in a method for halting bleeding in gingival tissue by placing the tip of the applicator device against the tissue, dispensing the hemostatic composition into the tissue, and burnishing the tissue while simultaneously dispensing the composition under pressure so that the composition is sufficiently agitated to increase the hemostatic activity of the hemostatic agent. The composition of the invention may also be used in a method for controlling tissue fluid movement through gingival tissue in which the composition is applied with the applicator device to the gingival tissue using the above method steps.

One aspect of the invention is an improved hemostatic dental composition for treating gingival areas to stop bleeding or provide tissue fluid control. Another aspect of the invention is a system for treating gingival areas by using the above dental composition with an applicator device. A further aspect of the invention are methods for treating gingival areas using the hemostatic dental composition. Yet another aspect of the invention are compositions, systems, and methods for treating soft tissues in general.

From the foregoing, it will be appreciated that an object of the invention is to provide an improved hemostatic dental composition for treating gingival areas to stop bleeding during dental procedures, which does not aggressively remove the smear layer on the dentin and smear layer plugs in dentinal tubules.

An additional object of the invention is to provide a composition that can provide complete sulcular and tissue fluid control, and which does not open up exposed dentinal tubules.

An additional object of the invention is to provide a composition that can provide complete sulcular and tissue fluid control prior to dental bonding procedures.

A further object of the invention is to provide methods for stopping bleeding and providing control of sulcular and tissue fluids, which minimize the trauma to teeth during dental reconstructive and restorative procedures.

Another object of the invention is to provide hemostatic compositions that are useful in providing hemostasis but which are more gentle and less aggressive when used in treating wounds in soft tissues in general.

These and other objects and features of the present invention will become more fully apparent from the following description and appended claims, or may be learned by the practice of the invention as set forth hereinafter.

DETAILED DESCRIPTION OF THE INVENTION

The present invention is an improved hemostatic dental composition for treating gingival areas of a tooth to stop bleeding and also to reduce sulcular fluid movement through the gingival epithelial tissue. In addition, the hemostatic compositions are more gentle and less aggressive when used to treat wounds and soft tissues in general. The hemostatic composition includes a hemostatic agent, a chemical agent for reducing the acidic effect or reactivity of the active chemical ingredient of the hemostatic agent, and an aqueous base.

In order to better understand the usefulness and function of the composition of the invention, a basic understanding of tooth structure is important. A tooth includes three regions known as the crown, neck, and root. Gingiva or gum is the soft tissue covering the neck of the tooth. The crown of the tooth is above the gum line and the root is embedded in a socket of the jaw bone. A pulp chamber or cavity is located inside of the tooth and extends from the crown to the root of the tooth. The pulp chamber contains dental pulp which is loose connective tissue containing cells, nerves, blood, lymph vessels, and connective tissues. Dentin surrounds the pulp chamber and contains about 50% collagen and about 50% calcium minerals. Within the dentin are dentinal tubules, which are microscopic canals that extend from the pulp chamber to the surface of the dentin. There are about 35,000 dentinal tubules per square millimeter of surface area on the dentin with each dentinal tubule having a diameter of about 1–3 microns. Since the dentinal tubules communicate with the pulp chamber and also contain plasma-type fluids under pressure, the sensation of pain and pressure can be transmitted to the nerve endings within the pulp chamber via the dentinal tubules. The dentinal tubules are occupied by odontoblastic processes. Odontoblasts are cells forming the surface layer of the dental papilla, which gives rise to dentin and dental pulp in a tooth. These cells line the pulp chamber and continue to provide dentin growth towards the pulp for years after a tooth has erupted.

When a tooth has been damaged it is often necessary to attach a dental prosthetic such as a crown over the damaged tooth. In order to apply the crown to the tooth, the enamel covering the dentin of the tooth must be shaped in order to prepare a surface for application of the crown. As discussed above, a newly prepared tooth has a smear layer on the surface of the dentin. Part of the smear layer enters the dentinal tubules, which open at the surface of the dentin, and forms plugs that occlude the tubules. The smear layer plugs in the dentinal tubules can provide a barrier that prevents harmful contaminants from entering the tubules and infecting the tooth before a temporary or permanent crown is attached. Any trauma or infection trauma of a tooth can cause damage to a tooth, which is cumulative, and can lead to death of the tooth.

In preparing a crown for a tooth, it is important to stop oral bleeding in order to take an accurate impression of the tooth. Once bleeding has been stopped, an impression material can be substantially contacted with the surface of the tooth and surrounding tissue, including crevices and indentations therein so that a well fitting crown can be created. An inaccurate impression is one of the main impediments to good sealing between the crown and the dentin and/or enamel surface, as well as the main impediment to a quality fitting crown. If there is an improper fit, then there is a poor seal and covering of the tooth, and the crown is more likely to prematurely fail or in some cases the surrounding supporting soft and/or hard tissues are likely to fail.

By using the hemostatic dental composition of the present invention during dental restorative and reconstructive procedures, bleeding can be stopped so that an accurate impression of a tooth can be made. The hemostatic composition also has the surprising and unexpected result of protecting dentin by maintaining the smear layer plugs in the dentinal tubules even after extended exposure times to the composition, and has a less aggressive nature on soft tissues. This dentin protecting effect is superior to an equal amount of the same active ingredient chemical hemostat not containing the other ingredients of the composition of the invention. The smear layer plugs in the dentinal tubules thus remain intact to occlude passage of potential contaminants into the tubules, thereby preventing sensitivity and/or infection of the tooth and providing protection to the tooth pulp by reducing potential trauma to the tooth. Thus, while the composition of the invention provides control of bleeding and enhances soft tissue retraction, the composition has the added benefit of reducing the aggressive nature of hemostatic and astringent chemicals on dental tissues.

Soft tissues in general are sensitive to caustic agents such as acids. While astringents are useful in checking the bleeding of wounds in soft tissues, they can cause inflammation and other patient discomforts or irritation. This is because most hemostatic agents tend to be quite acidic. Hence, the present invention also provides compositions and methods for providing hemostasis in all soft tissues, while being more gentle and less aggressive on the soft tissues.

The hemostatic agent used in the composition of the invention can be selected from a wide variety of hemostatic and astringent compounds, which can be used singly or in a variety of mixtures. These can include various metal salts such as the salts of aluminum, iron, zinc, manganese, bismuth, etc., as well as other salts containing these metals such as permanganates. Nonlimiting examples of suitable hemostatic agents include ferric sulphate, ferric subsulphate, ferric chloride, zinc chloride, aluminum chloride, aluminum sulfate, aluminum chlorohydrate, and aluminum acetate. Alums such as aluminum potassium sulfate and aluminum ammonium sulfate may also be used. In addition, tannins or other related polyphenolic compounds may be used as the hemostatic agent. The above astringent and hemostatic compounds are acidic in nature and typically have a pH from about 0 to 4.

A preferred hemostatic agent for use in the composition of the invention is a ferric salt compound. Preferred ferric salts include ferric sulphate, which has the formula $Fe_2(SO_4)_3$, and ferric subsulphate, which has the formula $Fe_4(OH)_2(SO_4)_5$. Both ferric and sulfate ions are present within the human body, thus the probability of allergic reactions to ferric sulfate or ferric subsulphate is extremely low. The ferric salts are coagulative hemostats and when contacted with blood, the ferric salts cause instant precipitation of blood proteins, thereby forming a coagulum.

The hemostatic agent also facilitates tissue retraction by reducing the elasticity of collagen fibers within the gingival cuff, thus preventing premature closure of the sulcular space during impression placement and solidification. In addition, the hemostatic agent facilitates reduced sulcular fluid movement through intact epithelium, whether for impression making or at bonding and luting stages of final restoration placement. Finally, the hemostatic agent is useful in stopping the bleeding of wounds in soft tissues in general.

The hemostatic agent present in the hemostatic composition is used in an effective amount sufficient enough to provide hemostatic properties to the composition. A preferred amount of the hemostatic agent is from about 1 to 40 percent by weight of the composition, and more preferably from about 10 to 30 percent by weight.

In order to counteract the acidic and other chemical effects of the hemostatic agent, a chemical agent having absorbing, binding, or coating properties is used in the hemostatic composition. The chemical agent can be selected from an inorganic filler, a high molecular weight polyol, or mixtures thereof. The chemical agent absorbs, loosely binds, or coats the hemostatic active ingredient chemical so that it will be less reactive on the smear layer in the dentinal tubules that come into contact with the hemostatic composition. The chemical agent essentially prevents direct contact of the total quantity of the active hemostatic ingredient in the composition with a tooth surface, thus diminishing the total available chemistries that would effect the smear layer removal. This prevents the acidic nature of the hemostatic agent from dissolving the smear layer plugs in the dentinal tubules, but does not interfere with the hemostatic properties of the hemostatic agent when contacted with an area to be treated, particularly when used with the Dento-Infusor device (discussed in detail below). This device via mechanical agitation selectively activates greater potential of needed chemistries for hemostasis at the location where activity is needed such as the site of bleeding.

The smear layer plugs in the dentinal tubules will thus remain substantially intact during treatment with the hemostatic composition to occlude passage of potential contaminants into the tubules. While the chemical agent in the composition primarily reduces the aggressive nature of the hemostatic agent on dental and surrounding tissue, the chemical agent also provides additional benefits such as reducing the unpleasant chemical exposure of the hemostatic agent to taste receptors, thereby reducing unpleasant taste sensations. The chemical agent having absorbing, binding, or coating properties is believed to render the hemostatic compositions less aggressive and more gentle when used to treat soft tissues in general.

A preferred inorganic filler is a silica-based absorbing agent such as colloidal silicas, fumed silicas, ground silicas, precipitated silicas, or mixtures thereof. The silica-based absorbing agent provides thixotropic properties to the hemostatic composition, resulting in shear thinning at the point of agitation, and thickening when agitation ceases which causes the hemostatic composition to become more viscous. This provides improved application control of the hemostatic composition when applied using an applicator device such as the Dento-Infusor device, over prior nonviscous hemostatic solutions and helps to keep the composition in place where applied.

Other inorganic fillers can also be used in the composition of the invention as long as they provide the absorbing or binding effect on the hemostatic agent. Examples of other useful inorganic fillers include metal oxides such as aluminum oxide and titanium dioxide. The inorganic filler acts as a binding agent toward the hemostatic agent in the composition.

A proposed theory for the mechanism of how the inorganic filler such as silica ($SiO_2$) binds the hemostatic agent such as a ferric salt follows. Particles of silica terminate with silanol (SiOH) groups on the particle surface. The hydroxide groups on the silanol have an affinity with the hydronium ions present in the aqueous ferric salt solution so that the hydroxide groups weakly hydrogen bond with neighboring hydronium ions. This hydrogen bonding theoretically should help bind up the aggressive acidic nature of the ferric salt solution, albeit the activity would increase if the composition is agitated. It is also believed that the silica has mechanical binding properties and acts as a "sponge" that physically absorbs the hemostatic agent. Thus, the silica reduces the acidic and other chemical effects of the hemostatic agent such as ferric salts by reducing the liquid hemostat activity until agitated, so that the hemostatic agent is less reactive toward dental and surrounding tissues that are passively contacted therewith. The hemostatic agent is also believed to be less aggressive on soft tissues by the same mechanism.

When the hemostatic composition is applied and rubbed on bleeding tissue, which is discussed in more detail below, the mechanical action or agitation releases the hemostat from its bound or absorbed state, increasing the hemostatic activity of the composition. Any extraneous hemostatic composition that comes into passive contact with other soft tissues, including dental tissue, has reduced activity. This significantly prevents dissolving of the smear layer in dentinal tubules and reduces other possible damage to surrounding tissues.

Various polyols, preferably of higher molecular weight, can be used as the chemical agent for reducing the acidic or other chemical activity of the hemostatic agent. The polyols act as a lubricant for the composition, as well as an organic coating agent that functions as a partial reaction suppressor for the hemostatic agent. The polyols can enhance the composition in suppressing the activity of the hemostatic agent by providing reduced reactivity potentials. Examples of suitable polyols include polyethylene glycol, glycerine, propylene glycol, dipropylene glycol, sorbitol, and the like. The polyols used can have a wide variety of molecular weights, depending on the rheology of the particular polyol at a given molecular weight (m.w.) and concentration relative to the other components and their concentrations. Raising the molecular weight of the polyol has the primary purpose of increasing the tendency of the polyol to coat the hemostatic agent in order to decrease the negative tissue effects thereof (e.g., reducing the caustic effect of otherwise uncoated or unshielded hydronium ions present in the hemostatic compositions). In general, as the concentration of the polyol is decreased, it will be preferable to increase the molecular weight of the polyol to obtain the same beneficial coating effect. Increasing the molecular weight of the polyol being used will generally increase the coating effect A preferred polyol for use in the hemostatic composition is polyethylene glycol. It has been found that high molecular weight polyols such as polyethylene glycols having an average molecular weight of at least about 600 are preferred, with an average molecular weight of at least about 1000 being more preferred, and an average molecular weight of at least about 1500 being most preferred. Nevertheless, it should be understood that polyols having an average molecular weight up to about 100,000 or more may be used. In some cases it is preferable to mix together two or more polyethylene glycols having varying average molecular weights (e.g., a mixture of polyethylene glycols having average molecular weights of 1500 and 8000, respectively).

The foregoing average molecular weight values for polyols such as polyethylene glycols were determined by titrating a given polyethylene glycol sample, which was first reacted with a phthalic anhydride-pyridine reagent, with an aqueous sodium hydroxide solution. In particular, the sample was reacted with a reagent consisting of 48 g of c.p. phthalic anhydride dissolved into 300 g of freshly distilled pyridine, after which 7 g of c.p. imidazole was added and the resulting mixture allowed to stand overnight. An amount of the sample equivalent to the expected molecular weight divided by 160 was added to 25 ml of the phthalic anhydride-pyridine reagent and the mixture was maintained at $98°±2°$ C. for 30 minutes. The mixture was cooled and then 10 ml of distilled water added. After 2 minutes, 0.5 ml of a 1.0% solution of phenolphthalein in pyridine was added as an indicator.

The resulting solution was titrated with standard 0.5N sodium hydroxide to a pink endpoint permanent for at least 15 seconds. A blank comprising 25 ml of the phthalic anhydride-pyridine reagent was also titrated. The average molecular weight of the polyethylene glycol was then calculated using the following equation:

$$\frac{g(sample) \times 2 \times 1000}{(B-A)N} = \text{average molecular weight}$$

A=ml of N normal NaOH required for the polyethylene glycol sample

B=average ml of N normal NaOH required for the blank

The foregoing test is set forth in more detail in the Union Carbide Product Information Bulletin for CARBOWAX® polyethylene glycols (1986), which lists other physical characteristics of polyethylene glycols based on varying molecular weight (such as density, melting or freezing range, solubility in water, average number of repeating oxyethylene units, etc.). For purposes of disclosure, the foregoing reference is incorporated herein by specific reference.

A proposed theory for the mechanism of how a polyol acts as a partial reaction suppressor toward the hemostatic agent follows. A polyol such as polyethylene glycol is an organic macro molecule that does not have astringent properties. The hemostatic agent such as ferric salts are inorganic molecules that have astringent and acidic properties. The polyethylene glycol partially covers the ferric salts with an organic coating or competes with these inorganic molecules to reduce or suppress the acidic and/or chemical activity of the ferric salts. The polyethylene glycol thereby reduces passive reactive contact of the ferric salts with dental tissue and the resulting smear layer removal effect. Agitating the composition will raise the probability that the astringent ferric salts will increase in activity and/or exposure with the desired areas to be treated and perform their function.

The chemical agent such as the inorganic filler or polyol is present in an effective amount for reducing the acidic or other chemical activity of the hemostatic agent without interfering with the astringent or hemostatic properties of the hemostatic agent as needed and/or as provided at appropriate agitation of the composition. A preferred amount of the chemical agent is from about 0.1 to 80 percent by weight of the composition, and more preferably from about 0.1 to 50 percent by weight. When the inorganic filler is used in the composition of the invention, a preferred amount is from about 0.1 to 30 percent by weight of the composition, and more preferably from about 0.1 to 10 percent by weight. When the polyol is used in the composition of the invention, a preferred amount is from about 0.1 to 50 percent by weight of the composition, and more preferably from about 5 to 40 percent by weight.

An aqueous base such as water is included in the hemostatic composition in an amount effective to provide a desired viscosity to the composition and to aid in dispersal and/or solution of the components. The water can be present in the other components of the composition or can be added separately. The water is preferably deionized prior to use in the composition. The aqueous base is present in the hemostatic composition in an amount from about 1 to 80 percent by weight of the composition, and preferably from about 40 to 60 percent by weight.

The above components may be mixed together in the desired amounts using standard mixing procedures to form the composition of the invention. If a solid hemostatic agent, such as a solid ferric salt, is used in formulating the composition of the invention, it is preferable to first dissolve the solid hemostatic agent in water before adding the other components of the composition.

A preferred modality for applying the hemostatic composition of the invention to dental tissue or other soft tissue is to use an applicator device that permits infusion and agitation of the hemostatic composition. A useful applicator device is disclosed in U.S. Pat. No. 4,578,055, the disclosure of which is incorporated herein by specific reference. The applicator device includes a hollow metal or plastic curved tube with a padded tip at one end. The padded tip is shaped so that it approximates the tissue sufficiently close to create a partial seal with the tissue. The curved tube is attached to a syringe-type dispenser for delivery of the hemostatic composition. A preferred applicator device with the above construction for use in the present invention is the Dento-Infusor device available from Ultradent Products, Inc., of South Jordan, Utah.

The Dento-Infisor device attached to a syringe containing the hemostatic composition is rubbed firmly against a cut surface, which permits a steady, gentle infusion of the hemostatic composition to a small area to control bleeding. If used with this device, the hemostatic composition is simply loaded into the syringe, or prefilled capsules are employed. The tip of the applicator is then inserted into the bleeding wound site, be it a cut, gingival sulcus, pulp chambers (as in pulpotomies on primary teeth) or the like. By "burnishing" or rubbing the end of the applicator at the same time the solution is deposited the bleeding can readily be controlled. Sufficient pressure is applied to the syringe plunger, while rubbing, to overcome the capillary blood flow, thus moving the hemostatic composition into the capillary orifices and subsurface tissues. This, as well as agitation with the resultant release of greater chemical activity of the composition as described above, induces coagulation within the capillary orifices, producing a bloodless field. The rubbing motion on the tissue also removes extraneous coagulum that extends beyond the tissue surface while enhancing formation of coagulum plugs at the capillary orifices of the soft tissue.

Hemostasis is achieved when there is control of sulcular hemorrhage such that bleeding does not recur as soon as the gingival tissues are touched or manipulated. This is known as "active" hemostasis, which is in contrast to the "passive" hemostasis of other procedures in which seepage can occur at will or quite commonly just before or during the placement of impression material into the sulcus. Depending on the patient's periodontal and systemic health, "active" hemostasis may be obtained using the procedures of the invention with as little as 2 to 3 or up to as many as 20 to 30 passes around the sulcus. Small areas of persistent bleeding can be controlled by applying firm pressure against the offending area with the Dento-Infusor device for 2 to 4 seconds as the syringe plunger is slowly depressed.

Premature drying of the prepared tooth surface and gingival tissues will cause extraneous coagulum to adhere to the surfaces, while over vacuuming can sometimes cause unwanted drying. A light drizzle of water applied to the area as the hemostatic composition is applied will minimize the risk of coagulative debris adhesion. This also minimizes chemical exposure to hard and soft tissues and maintains a clean field. The presence of extraneous coagulum, however does not impede the hemostatic process, since pressure on the syringe assures that fresh hemostatic composition will reach the capillary orifices. The presence of the hemostatic composition in the sulcus without formation of new coagulum indicates that hemostasis has been achieved. Upon hemostasis, the area is rinsed and cleaned. A thorough, firm, air/water spray facilitates coagulum removal and confirms the quality of the hemostasis. If bleeding occurs during this firm rinsing procedure, it would most likely occur during the impression making or restorative procedure, thus interfering with the procedure. If hemorrhage or seepage is identified, the infusing process is repeated until all bleeding is arrested.

With this technique, the clinician can take time to verify that the entire margin and sulcus are clean and visible. All margins should be clean and exposed before impression material is extruded into the sulcus. Impression material is then mixed and syringed around the sulcus in a calm and unhurried manner, since a quality impression can be made each time. By using the above tissue management procedures, an accurate and complete impression with good marginal detail can be expected even for multiple preparations. The above procedures virtually eliminate the stress caused by other techniques, in which split-second timing is required to prevent oozing into the sulcus and contamination of the prepared tooth surface.

The hemostatic composition of the invention can also be used with an applicator such as the Dento-Infusor device to reduce sulcular fluid movement through intact epithelium during bonding and luting stages of final restoration placement such as cementing a crown on a tooth. Any extraneous oral fluids present during the adhesive process can lead to failure or discolorations of the restoration. Thus, using the hemostatic composition to reduce sulcular fluid movement can prevent these problems.

All near gingival or subgingival bonded restorations have margins that are susceptible to sulcular fluid contamination during bonding and luting procedures. In adhesive dentistry, all prepared tooth surfaces, especially the margins, must be isolated from tissue fluids such as blood and/or sulcular fluids. The hemostatic composition of the invention can be used to reduce or eliminate permeability of the sulcular epithelium in addition to acting as a hemostatic agent, thus preventing sulcular tissue fluid flow. If sulcular tissue fluid flow is present or there is bleeding prior to bonding of restorations, the hemostatic composition of the invention can be used with the Dento-Infusor device to arrest flow of the blood or other fluids with minimal effect on surrounding tissues.

The permeability of the sulcular epithelium with resultant sulcular tissue fluid flow is eliminated or greatly reduced by gently rubbing the sulcular tissues with the hemostatic composition via the Dento-Infusor device, which is preferably made of a plastic material. The sulcus is firmly rinsed and noted for dryness. Bonding technique steps can then be performed, from acid conditioning to priming to coating with resins, all of which can occur uneventfully since the sulcular fluids have been controlled. By providing sulcular fluid control and good cleaning prior to bonding, a good bond and seal for the restoration is assured, preventing future problems related to leaking of the restorations which can result in leakage and discoloration thereof.

In addition, the hemostatic composition of the invention can be applied to dental tissue using a number of different methods and devices that are known to those of ordinary skill in the art.

The following examples set forth various hemostatic compositions within the scope of the present invention. These examples are intended to be purely exemplary and should not be viewed as limiting the scope of the invention.

EXAMPLE 1

A hemostatic composition of the invention was made by mixing the ingredients in the amounts listed below:

| Ingredient | Amount (Weight %) |
| --- | --- |
| Ferric Sulphate | 34.4 |
| Deionized Water | 53.2 |
| Polyethylene Glycol (8000 m.w.) | 9 |
| Fumed Silica | 3.4 |

The above components formed a hemostatic composition that was effective in stopping bleeding and preventing sulcular tissue fluid flow, without opening up dentinal tubules. The hemostatic composition left the smear layer plugs in the dentinal tubules substantially intact.

EXAMPLE 2

A hemostatic composition of the invention was made by mixing the ingredients in the amounts listed below:

| Ingredient | Amount (Weight %) |
| --- | --- |
| Ferric Sulphate | 22.7 |
| Deionized Water | 47.9 |
| Polyethylene Glycol (1500 m.w.) | 26 |
| Fumed Silica | 3.4 |

The above components formed a hemostatic composition that was effective in stopping bleeding and preventing sulcular tissue fluid flow, without opening up dentinal tubules. The hemostatic composition left the smear layer plugs in the dentinal tubules substantially intact.

EXAMPLE 3

A hemostatic composition of the invention was made by mixing the ingredients in the amounts listed below:

| Ingredient | Amount (Weight %) |
| --- | --- |
| Ferric Sulphate | 20.6 |
| Deionized Water | 32.7 |
| Polyethylene Glycol (8000 m.w.) | 32.3 |
| Polyethylene Glycol (1450 m.w.) | 11.3 |
| Fumed Silica | 3.1 |

The above components formed a hemostatic composition that was effective in stopping bleeding and preventing sulcular tissue fluid flow, without opening up dentinal tubules. The hemostatic composition left the smear layer plugs in the dentinal tubules substantially intact.

EXAMPLE 4

A hemostatic composition of the invention is made by mixing the ingredients in the amounts listed below:

| Ingredient | Amount (Weight %) |
| --- | --- |
| Ferric Sulphate | 22.7 |
| Deionized Water | 52.9 |
| Polyethylene Glycol (8000 m.w.) | 21 |
| Fumed Silica | 3.4 |

The above components form a hemostatic composition that is effective in stopping bleeding and preventing sulcular tissue fluid flow, without opening up dentinal tubules. The hemostatic composition will leave the smear layer plugs in the dentinal tubules substantially intact.

EXAMPLE 5

A hemostatic composition of the invention is made by mixing the ingredients in the amounts listed below:

| Ingredient | Amount (Weight %) |
| --- | --- |
| Aluminum Chloride | 22.7 |
| Deionized Water | 52.9 |
| Polyethylene Glycol (8000 m.w.) | 21 |
| Fumed Silica | 3.4 |

The above components form a hemostatic composition that is effective in stopping bleeding and preventing sulcular tissue fluid flow, without opening up dentinal tubules. The hemostatic composition will leave the smear layer plugs in the dentinal tubules substantially intact.

EXAMPLE 6

A hemostatic composition of the invention is made by mixing the ingredients in the amounts listed below:

| Ingredient | Amount (Weight %) |
| --- | --- |
| Ferric Sulphate | 10 |
| Deionized Water | 77.6 |
| Polyethylene Glycol (8000 m.w.) | 2.4 |
| Fumed Silica | 10 |

The above components form a hemostatic composition that is effective in stopping bleeding and preventing sulcular tissue fluid flow, without opening up dentinal tubules. The hemostatic composition will leave the smear layer plugs in the dentinal tubules substantially intact.

EXAMPLE 7

A hemostatic composition of the invention is made by mixing the ingredients in the amounts listed below:

| Ingredient | Amount (Weight %) |
| --- | --- |
| Ferric sulphate | 34.4 |
| Deionized Water | 51.2 |

| Ingredient | Amount (Weight %) |
|---|---|
| Polyethylene Glycol (8000 m.w.) | 13.9 |
| Fumed silica | 0.5 |

The above components form a hemostatic composition that is effective in stopping bleeding and preventing sulcular tissue fluid flow, without opening up dentinal tubules. The hemostatic composition will leave the smear layer plugs in the dentinal tubules substantially intact.

EXAMPLE 8

A hemostatic composition of the invention is made by mixing the ingredients in the amounts listed below:

| Ingredient | Amount (Weight %) |
|---|---|
| Ferric Sulphate | 20 |
| Deionized Water | 65 |
| Fumed Silica | 15 |

The above components form a hemostatic composition that is effective in stopping bleeding and preventing sulcular tissue fluid flow, without opening up dentinal tubules. The hemostatic composition will leave the smear layer plugs in the dentinal tubules substantially intact.

EXAMPLE 9

A hemostatic composition of the invention is made by mixing the ingredients in the amounts listed below:

| Ingredient | Amount (Weight %) |
|---|---|
| Ferric Sulphate | 28 |
| Deionized Water | 63 |
| Fumed Silica | 9 |

The above components form a hemostatic composition that is effective in stopping bleeding and preventing sulcular tissue fluid flow, without opening up dentinal tubules. The hemostatic composition will leave the smear layer plugs in the dentinal tubules substantially intact.

EXAMPLE 10

A hemostatic composition of the invention is made by mixing the ingredients in the amounts listed below:

| Ingredient | Amount (Weight %) |
|---|---|
| Ferric Sulphate | 20 |
| Deionized Water | 75 |
| Fumed Silica | 5 |

The above components form a hemostatic composition that is effective in stopping bleeding and preventing sulcular tissue fluid flow, without opening up dentinal tubules. The hemostatic composition will leave the smear layer plugs in the dentinal tubules substantially intact.

EXAMPLE 11

A hemostatic composition of the invention is made by mixing the ingredients in the amounts listed below:

| Ingredient | Amount (Weight %) |
|---|---|
| Ferric Sulphate | 18 |
| Deionized Water | 79 |
| Fumed Silica | 3 |

The above components form a hemostatic composition that is effective in stopping bleeding and preventing sulcular tissue fluid flow, without opening up dentinal tubules. The hemostatic composition will leave the smear layer plugs in the dentinal tubules substantially intact.

EXAMPLE 12

A hemostatic composition of the invention was made by mixing the ingredients in the amounts listed below:

| Ingredient | Amount (Weight %) |
|---|---|
| Ferric Sulphate | 20 |
| Deionized Water | 54 |
| Polyethylene Glycol (8000 m.w.) | 26 |

The above components formed a hemostatic composition that was effective in stopping bleeding and preventing sulcular tissue fluid flow, without opening up dentinal tubules. The hemostatic composition left the smear layer plugs in the dentinal tubules substantially intact.

EXAMPLE 13

A hemostatic composition of the invention is made by mixing the ingredients in the amounts listed below:

| Ingredient | Amount (Weight %) |
|---|---|
| Aluminum Chloride | 18 |
| Deionized Water | 37 |
| Polyethylene Glycol (8000 m.w.) | 45 |

The above components form a hemostatic composition that is effective in stopping bleeding and preventing sulcular tissue fluid flow, without opening up dentinal tubules. The hemostatic composition will leave the smear layer plugs in the dentinal tubules substantially intact.

EXAMPLE 14

A hemostatic composition of the invention is made by mixing the ingredients in the amounts listed below:

| Ingredient | Amount (Weight %) |
|---|---|
| Ferric Sulphate | 20 |
| Deionized Water | 54 |
| Polyethylene Glycol (1500 m.w.) | 26 |

The above components form a hemostatic composition that is effective in stopping bleeding and preventing sulcular tissue fluid flow, without opening up dentinal tubules. The hemostatic composition will leave the smear layer plugs in the dentinal tubules substantially intact.

EXAMPLE 15

A hemostatic composition of the invention is made by mixing the ingredients in the amounts listed below:

| Ingredient | Amount (Weight %) |
| --- | --- |
| Ferric Sulphate | 15 |
| Deionized Water | 25 |
| Polyethylene Glycol (8000 m.w.) | 30 |
| Polyethylene Glycol (1500 m.w.) | 30 |

The above components form a hemostatic composition that is effective in stopping bleeding and preventing sulcular tissue fluid flow, without opening up dentinal tubules. The hemostatic composition will leave the smear layer plugs in the dentinal tubules substantially intact.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes that come within the meaning and range of equivalency of the claims are to be embraced within their scope.

What is claimed and desired to be secured by United States Letters Patent is:

1. A hemostatic composition comprising:
   (a) a quantity of a hemostatic agent selected from the group consisting of ferric sulfate, ferric subsulfate, ferric chloride, zinc chloride, aluminum chloride, aluminum sulfate, aluminum chlorohydrate, aluminum acetate, alums, permanganates, tannins, and mixtures thereof;
   (b) an effective amount of an inorganic filler for increasing the viscosity of the hemostatic composition and for reducing acidic activity of the hemostatic agent;
   (c) a polyol for assisting the inorganic filler in reducing the acidic activity of the hemostatic agent, the polyol being selected from the group consisting of polyethylene glycol, propylene glycol, dipropylene glycol, polypropylene glycol, glycerine, sorbitol, and mixtures thereof; and
   (d) an aqueous base.

2. A hemostatic composition as defined in claim 1, wherein the hemostatic agent is present in an amount in a range from about 1% to about 40% by weight of the hemostatic composition.

3. A hemostatic composition as defined in claim 1, wherein the inorganic filler and polyol are present together in an amount in a range from about 0.2% to about 80% by weight of the hemostatic composition.

4. A hemostatic composition as defined in claim 1, wherein the inorganic filler is present in an amount in a range from about 0.1% to about 30% by weight of the hemostatic composition.

5. A hemostatic composition as defined in claim 1, wherein the inorganic filler comprises a silica-based absorbing agent.

6. A hemostatic composition as defined in claim 1, wherein the inorganic filler is selected from the group consisting of colloidal silica, fumed silica, ground silica, precipitated silica, aluminum oxide, titanium dioxide, and mixtures thereof.

7. A hemostatic composition as defined in claim 1, wherein the polyol has a molecular weight of at least about 600.

8. A hemostatic composition as defined in claim 1, wherein the polyol has a molecular weight greater than about 1000.

9. A hemostatic composition as defined in claim 1, wherein the hemostatic composition has increased hemostatic activity upon agitating the hemostatic composition.

10. A hemostatic composition comprising:
    (a) a quantity of a hemostatic agent selected from the group consisting of ferric sulfate, ferric subsulfate, ferric chloride, zinc chloride, aluminum chloride, aluminum sulfate, aluminum chlorohydrate, aluminum acetate, alums, permanganates, tannins, and mixtures thereof;
    (b) an effective amount of a high molecular weight polyol for increasing the viscosity of the hemostatic composition and for reducing acidic activity of the hemostatic agent, the high molecular weight polyol having a molecular weight of at least about 600 and being selected from the group consisting of polyethylene glycol, polypropylene glycol, and mixtures thereof; and
    (c) an aqueous base.

11. A hemostatic composition as defined in claim 10, wherein the hemostatic composition further includes an inorganic filler which assists the high molecular weight polyol in increasing the viscosity of the hemostatic composition and in reducing the acidic activity of the hemostatic agent.

12. A hemostatic composition as defined in claim 11, wherein the inorganic filler is selected from the group consisting of colloidal silica, fumed silica, ground silica, precipitated silica, aluminum oxide, titanium dioxide, and mixtures thereof.

13. A hemostatic composition as defined in claim 11, wherein the inorganic filler is present in an amount in a range from about 0.1% to about 30% by weight of the hemostatic composition.

14. A hemostatic composition as defined in claim 10, wherein the hemostatic agent is present in an amount in a range from about 1% to about 40% by weight of the hemostatic composition.

15. A hemostatic composition as defined in claim 10, wherein the high molecular weight polyol is present in an amount in a range from about 0.1% to about 50% by weight of the hemostatic composition.

16. A hemostatic composition as defined in claim 10, wherein the high molecular weight polyol has a molecular weight of at least about 1000.

17. A hemostatic composition as defined in claim 10, wherein the hemostatic composition has increased hemostatic activity upon agitating the hemostatic composition.

18. A hemostatic composition comprising:
    (a) a quantity of a hemostatic agent selected from the group consisting of ferric sulfate, ferric subsulfate, ferric chloride, zinc chloride, aluminum chloride, aluminum sulfate, aluminum chlorohydrate, aluminum acetate, alums, permanganates, tannins, and mixtures thereof;
    (b) an effective amount of an inorganic filler for increasing the viscosity of the hemostatic composition and for reducing acidic activity of the hemostatic agent;
    (c) a polyol for assisting the inorganic filler in increasing the viscosity of the hemostatic composition and in reducing the acidic activity of the hemostatic agent, the polyol having a molecular weight greater than about 600 and being selected from the group consisting of polyethylene glycol, polypropylene glycol, and mixtures thereof; and
    (d) an aqueous base.

19. A hemostatic composition as defined in claim 18, wherein the hemostatic agent is included in an amount in a range from about 1% to about 40% by weight of the hemostatic composition.

20. A hemostatic composition as defined in claim 18, wherein the inorganic filler is included in an amount in a range from about 0.1% to about 30% by weight of the hemostatic composition.

21. A hemostatic composition as defined in claim 18, wherein the inorganic filler is a silica-based absorbing agent.

22. A hemostatic composition as defined in claim 18, wherein the inorganic filler is selected from the group consisting of colloidal silica, fumed silica, ground silica, precipitated silica, aluminum oxide, titanium dioxide, and mixtures thereof.

23. A hemostatic composition as defined in claim 18, wherein the hemostatic composition has increased hemostatic activity upon agitating the hemostatic composition.

24. A hemostatic composition as defined in claim 18, wherein the polyol has a molecular weight greater than about 1000.

25. A hemostatic composition comprising:
   (a) a ferric salt compound in an amount in a range from about 1% to about 40% by weight of the hemostatic composition;
   (b) a silica-based absorbing agent in an amount in a range from about 0.1% to about 30% by weight of the hemostatic composition;
   (c) a polyol selected from the group consisting of polyethylene glycol, propylene glycol, dipropylene glycol, polypropylene glycol, glycerine, sorbitol, and mixtures thereof, the polyol included in an amount in a range about 0.1% to about 50% by weight of the hemostatic composition; and
   (d) water in an amount in a range from about 1% to about 80% by weight of the hemostatic composition.

26. A hemostatic composition as defined in claim 25, wherein the ferric salt compound is selected from the group consisting of ferric sulfate, ferric subsulfate, ferric chloride, and mixtures thereof.

27. A hemostatic composition as defined in claim 25, wherein the silica-based absorbing agent is selected from the group consisting of colloidal silica, fumed silica, ground silica, precipitated silica, and mixtures thereof.

28. A hemostatic composition as defined in claim 25, wherein the polyol has a molecular weight greater than about 600.

29. A hemostatic composition as defined in claim 25, wherein the polyol has a molecular weight of at least about 1000.

30. A hemostatic composition as defined in claim 25, wherein the hemostatic composition has increased hemostatic activity upon agitating the hemostatic composition.

31. A system for promoting healing of wounds comprising:
   (a) a hemostatic composition including:
      (i) about 1% to about 40% by weight of a hemostatic agent selected from the group consisting of ferric sulfate, ferric subsulfate, ferric chloride, zinc chloride, aluminum chloride, aluminum sulfate, aluminum chlorohydrate, aluminum acetate, alums, permanganates, tannins, and mixtures thereof;
      (ii) about 0.1% to about 30% by weight of a silica-based absorbing agent;
      (iii) about 0.1% to about 50% by weight of a polyol selected from the group consisting of polyethylene glycol, propylene glycol, propylene glycol, dipropylene glycol, glycerine, sorbitol, and mixtures thereof; and
      (iv) a quantity of water; and
   (b) an applicator device capable of applying the hemostatic composition under pressure to an area of bleeding, the applicator device including a padded porous tip through which the hemostatic composition may be delivered to provide agitation of the hemostatic composition when applying the hemostatic tissue to the area of bleeding.

32. A system as defined in claim 31, wherein the silica-based absorbing agent is selected from the group consisting of colloidal silica, fumed silica, ground silica, precipitated silica, and mixtures thereof.

33. A system as defined in claim 31, wherein the polyol has a molecular weight of at least about 600.

34. A system as defined in claim 31, wherein the polyol has a molecular weight of at least about 1000.

35. A system as defined in claim 31, wherein the hemostatic composition has increased hemostatic activity upon agitating the hemostatic composition.

36. A method for stopping bleeding comprising the steps of:
   (a) placing an effective quantity of a hemostatic composition onto a bleeding or wounded area, the hemostatic composition having increased hemostatic activity upon agitating the hemostatic composition, the hemostatic composition including:
      (i) a quantity of a hemostatic agent selected from the group consisting of ferric sulfate, ferric subsulfate, ferric chloride, zinc chloride, aluminum chloride, aluminum sulfate, aluminum chlorohydrate, aluminum acetate, alums, permanganates, tannins, and mixtures thereof;
      (ii) an effective amount of an inorganic filler for increasing the viscosity of the hemostatic composition and for reducing acidic activity of the hemostatic agent;
      (iii) a polyol for assisting the inorganic filler in reducing the acidic activity of the hemostatic agent, the polyol being selected from the group consisting of polyethylene glycol, propylene glycol, dipropylene glycol, polypropylene glycol, glycerine, sorbitol, and mixtures thereof; and
      (iv) an aqueous base; and
   (b) burnishing the bleeding or wounded area so as to agitate the hemostatic composition to increase the hemostatic activity of the hemostatic composition.

37. A method as defined in claim 36, wherein the hemostatic agent is included in an amount in a range from about 1% to about 40% by weight of the hemostatic composition.

38. A method as defined in claim 36, wherein the inorganic filler and polyol are included in a combined amount in a range from about 0.1% to about 80% by weight of the hemostatic composition.

39. A method as defined in claim 36, wherein the inorganic filler is included in an amount in a range from about 0.1% to about 30% by weight of the hemostatic composition.

40. A method as defined in claim 36, wherein the inorganic filler is selected from the group consisting of colloidal silica, fumed silica, ground silica, precipitated silica, aluminum oxide, titanium dioxide, and mixtures thereof.

41. A method as defined in claim 36, wherein the polyol is included in an amount in a range from about 0.1% to about 50% by weight of the composition.

42. A method as defined in claim 36, wherein the polyol has a molecular weight of at least about 600.

43. A method as defined in claim 36, wherein the polyol has a molecular weight greater than about 1000.

* * * * *

UNITED STATES PATENT AND TRADEMARK OFFICE
CERTIFICATE OF CORRECTION

PATENT NO. : 5,785,955

DATED : July 28, 1998

INVENTOR(S) : Dan E. Fischer

It is certified that error appears in the above-identified patent and that said Letters Patent is hereby corrected as shown below:

Title    On the title page, item [54] and Column 1; Title is incorrect. Delete current title and replace with --IMPROVED HEMOSTATIC COMPOSITIONS FOR TREATING SOFT TISSUE--

Title page    second column. Article entitled "Hemostatics and Astringents" should read --Hemostatics and Astringents: Mineral Astringents--

Item [57]    last line of abstract, delete "affects" and replace with --effects--

Signed and Sealed this

Sixteenth Day of November, 1999

Attest:

Q. TODD DICKINSON

Attesting Officer    Acting Commissioner of Patents and Trademarks